United States Patent
Cho

(10) Patent No.: US 7,641,248 B2
(45) Date of Patent: Jan. 5, 2010

(54) COMPACT DOUBLE TWEEZERS

(76) Inventor: Yong-Hoon Cho, 604 Murfield Ct., Fullerton, CA (US) 92835

( * ) Notice: Subject to any disclaimer, the term of this patent is extended or adjusted under 35 U.S.C. 154(b) by 0 days.

(21) Appl. No.: 11/975,879

(22) Filed: Oct. 22, 2007

(65) Prior Publication Data

US 2009/0102214 A1    Apr. 23, 2009

(51) Int. Cl.
*B25B 9/02*    (2006.01)
(52) U.S. Cl. ............................ 294/99.2; 606/210
(58) Field of Classification Search ............ 294/3, 294/16, 99.2; 606/210, 211; 7/101, 118; D28/55
See application file for complete search history.

(56) References Cited

U.S. PATENT DOCUMENTS

| | | | | |
|---|---|---|---|---|
| 461,148 A | * | 10/1891 | Fisher | ............... 7/101 |
| 776,555 A | * | 12/1904 | Settle | ............... 269/6 |
| 1,842,403 A | | 1/1932 | Hunsaker et al. | |
| 2,334,252 A | | 11/1943 | Darling | |
| 2,579,207 A | * | 12/1951 | Scheib | ............... 29/766 |
| 4,841,819 A | * | 6/1989 | Williams | ............... 81/3.8 |
| 5,449,374 A | * | 9/1995 | Dunn et al. | ............... 606/208 |
| 5,740,611 A | * | 4/1998 | Schloss | ............... 30/29.5 |
| D448,118 S | * | 9/2001 | Grisoni | ............... D28/55 |
| D456,076 S | | 4/2002 | Tyler | |
| D521,685 S | | 5/2006 | Cho | |
| 2008/0125810 A1 | * | 5/2008 | Cho | ............... 606/211 |

* cited by examiner

*Primary Examiner*—Dean J Kramer
(74) *Attorney, Agent, or Firm*—Maria Erlinda Co Sarno

(57) ABSTRACT

Two tweezers which folds and unfolds relative to each other is connected by a central connector which allows the rotation of the tweezers without one tweezers rubbing into the other tweezers. Each tweezers has a tweezer head section extending to a base section. The base sections have an external base cover serving as handles for the tweezers. A cover shields the tweezer heads of the two tweezers. A spring assisted locator pin inserts and retracts from a hole as the tweezers positions back and forth from a folding position to an unfolding position.

20 Claims, 6 Drawing Sheets

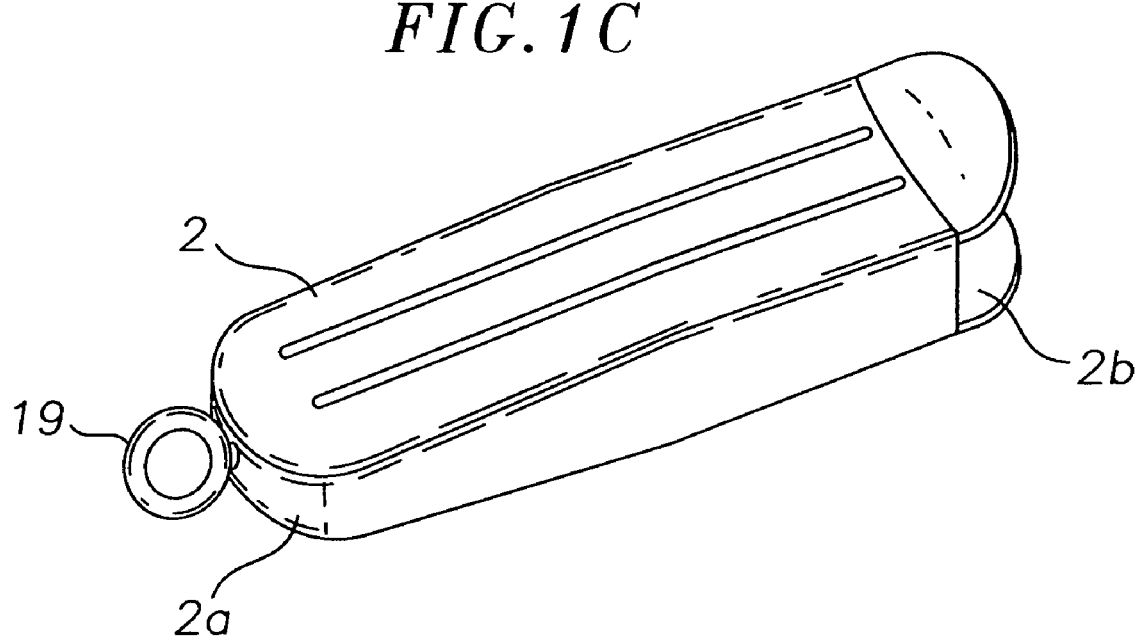
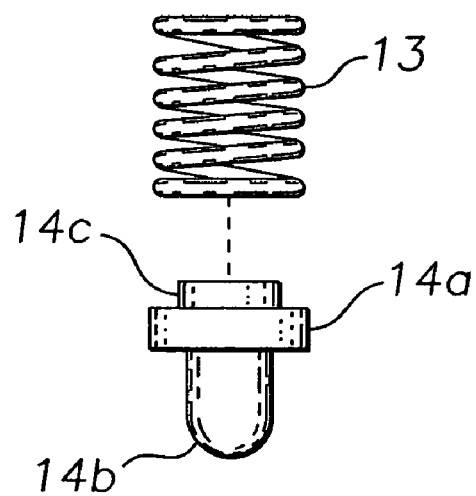

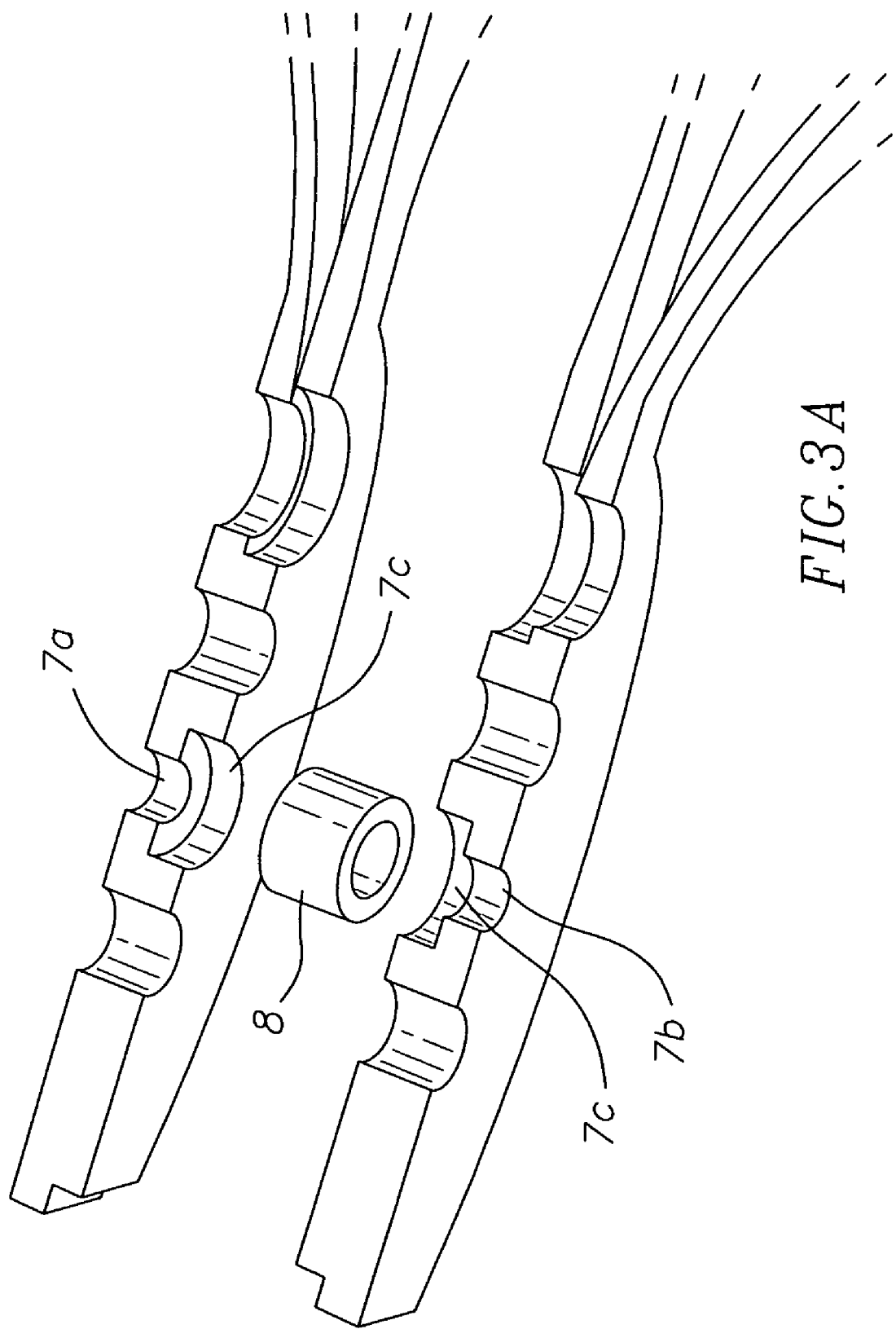

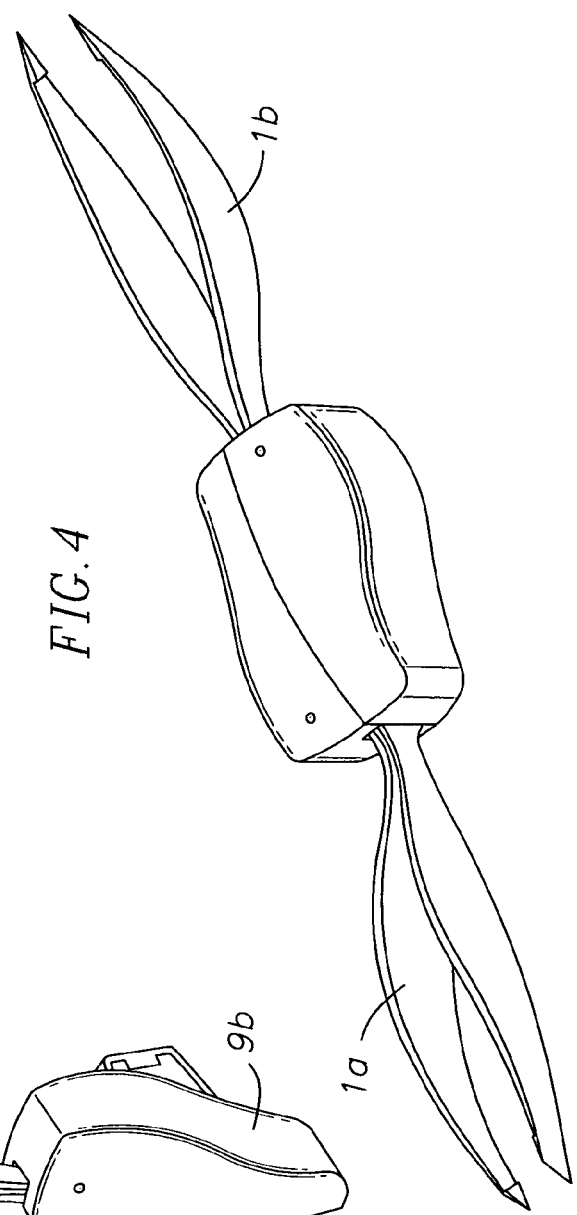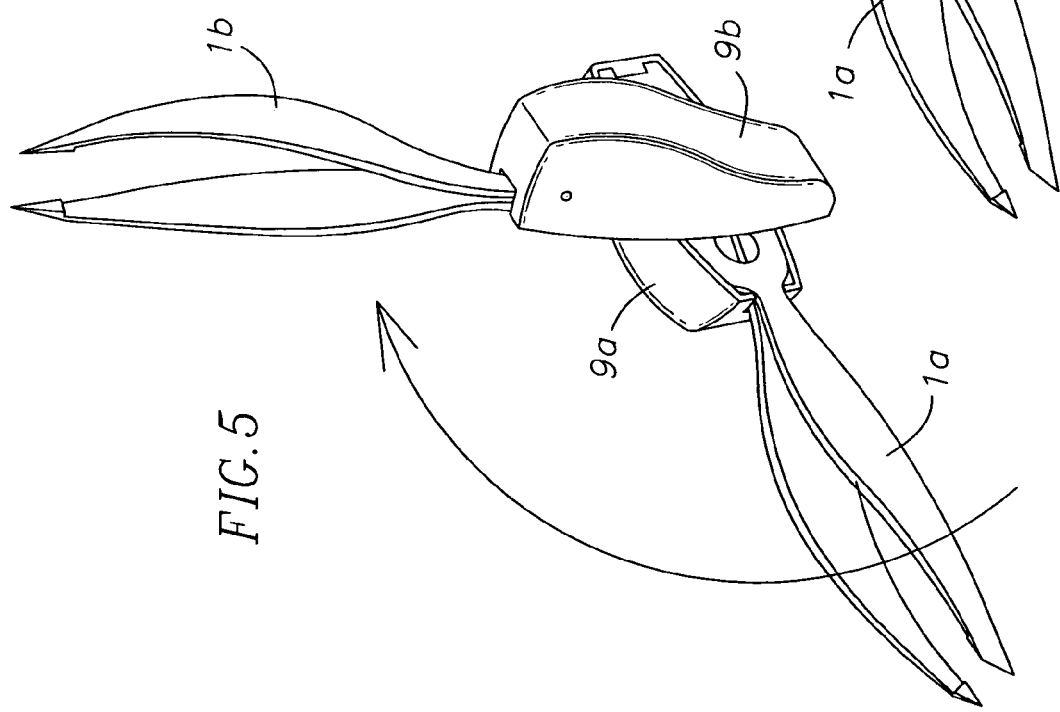

COMPACT DOUBLE TWEEZERS

This invention relates to a device having two tweezers with each tweezers capable of folding together, laying side by side, when not in use and unfolding, positioning opposite each other when in use.

BACKGROUND

Tweezers with a pair of pincers having identical or two different tips at each end are known. These tweezers are usually formed from two elongated flat sheets fused together midway resulting in a pair of free opposing ends. Darling (U.S. Pat. No. 2,334,252) discloses a double ended device in one unit with both ends presenting a pair of gripping jaws. Hunsaker (U.S. Pat. No. 1,842,403) has a tweezers at one end and another device of a related function such as a blackhead remover on the other. The end opposite the tweezers can have several types or arms by hingedly connecting these through a journal pin at said end. Inventor, Yong Hoon Cho (U.S. D521,685S) as well as Tyler (U.S. D456,076) have design patents on a double headed tweezers. Both of these design patents are also on two tweezer tips on a single tweezers at both free opposing ends which are aligned opposite each other.

These double ended tweezers are usually longer than a tweezers with a pair of tips at one end. Also, having two tips rather than one, there is more risk of hurting the users and bystanders especially children because both ends can have sharp tips that could injure through poking. This double ended tweezers can have a case to enclose and house the tweezers to prevent the device from hurting a person. Since the double ended tweezers is usually longer, the device may not easily fit a small pocket and would be less portable. Further, two covers are needed, one for each tip.

Two tweezer heads rather than one is desired because of the many variable usage of the tweezers and having two instead of one allows a user to just flip the tweezers during operations that require the use of two different tips. Having two identical tips is also desired to prevent cross contamination especially in microbiological and biochemical applications caused by using the same tip for different items. Tweezers have been used for different purposes such as for cosmetic purposes, usually for plucking unwanted hair; in surgery for removing splinters or for holding/gripping tissues, blood vessels, organs and the like; in dentistry for clamping a tooth; in weaving and embroidery for plucking or inserting a thread, etc. In these applications, the design of the tips usually cater to their respective applications. The tips can be slanted, straight, pointed, rounded, serrated, etc.

It is therefore an object of this invention to provide two tweezers with identical or different tips that can be folded and unfolded at will.

It is also an object of this invention to provide a covered two tweezers in a compact portable form so it can easily fit a small space or hanged along with keys and other items on a chain.

It is a further object of this invention to provide two tweezer at the same time for variable simultaneous usage.

SUMMARY OF THE INVENTION

This invention relates to a compact double tweezers that can fold or unfold relative to each other, comprising two tweezers, each having a head section including a pincer and a pair of tips and a base section having several holes for connection and engagement of parts of the double tweezers; a central connector connecting the two tweezers and allowing the tweezers to rotate relative to each other; an external base cover for each base section of the tweezers, the external base covers serving as handles for the tweezers; and, a locator pin inserted into a hole, the locator pin having a rounded tip on one end protruding from the hole and inserting into a second hole when the two tweezers are in one position and an annular stopper on another end situated on top of a spring inside a channel, the annular stopper having a diameter greater than the turn diameter of the spring pressing and compressing the spring when the rounded tip recedes towards the hole as the tweezers change position and releasing the spring when the rounded tip enters into a third hole when the two tweezers situate in another position. The device can have a cover or cap for shielding the head sections of the two tweezers. The cover or cap can have a ring attached to its closed end top to allow the compact double tweezers to be carried on a chain. The central connector has a liner at its mid section and this liner has an outside surface diameter greater than the central connector. The liner situates on a trough to keep the liner from moving along the central connector. The central connector forms a gap between the two tweezers to keep the tweezers from rubbing each other and for accommodating the protruding rounded tip of the locator pin. The annular stopper can have a protruding cylindrical piece opposite the rounded tip as shown in FIG. 3B or it can be a flat circular head as shown in FIG. 3. When the locator pin situates the two tweezers in a position, the hole where the rounded tip insert into aligns with the hole from where the rounded tip protrudes from. The tweezers change position when a twisting pressure is exerted on the external covers of the tweezers.

Other embodiments of the present invention will become readily apparent to those skilled in the art from the following detailed description, wherein it shows and describes only certain embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Aspects of the present invention are illustrated by way of example, and not by way of limitation, in the accompanying drawings, wherein:

FIG. 1A is a perspective view of a fully encased compact double tweezers and FIG. 1C shows a ring on the cover.

FIG. 1B is a perspective view of the double tweezers removed from the tweezer cover.

FIG. 3 is a cross section of the double tweezer of FIG. 1B without the cover or cap and FIG. 3B is an isolated view of the annular stopper with a protruding cylindrical piece opposite the rounded tip.

FIG. 3A is an exploded view detailing the hole or cavity where the liner on the central connector situates.

FIG. 4 shows the double tweezers in a fully unfolded position.

FIG. 5 shows the tweezers in a semi-unfolded position connected to their respective base covers after the spring is installed into the channel and engaged with a location pin.

DETAILED DESCRIPTION OF THE INVENTION

The detailed description represented herein is not intended to represent the only way or the only embodiment in which the claimed invention may be practiced. The description herein is provided merely as an example or examples or illustrations of the claimed invention and should not be construed as the only way or as preferred or advantageous over other embodiments or means of practicing the invention. Any two tweezers that can fold and unfold relative to each other is within the scope of this invention. The detailed description includes specific details to provide a thorough understanding of the claimed invention and it is apparent to those skilled in the art that the claimed invention may be practiced without these specific details. In some instances, well known structures and devices may be shown in block diagrams or drawn with broken lines in order to either avoid obscuring the main concepts of the invention or to show the relationship of one part to the other.

To make two tweezers fit into a small space, the tweezers can be made to fold when not in use and to unfold when in use. Folding here means a position when the two tweezers situate side by side with their tips facing the same direction while unfolding means a position when the two tweezers situate horizontally with their tips facing opposite each other. Folding and unfolding of the two tweezers are accomplished by rotating one tweezer relative to the other through a twisting action. To prevent the tips from hurting someone, it is recommended to provide a cap to shield the tips.

Figures 1A, 1B:
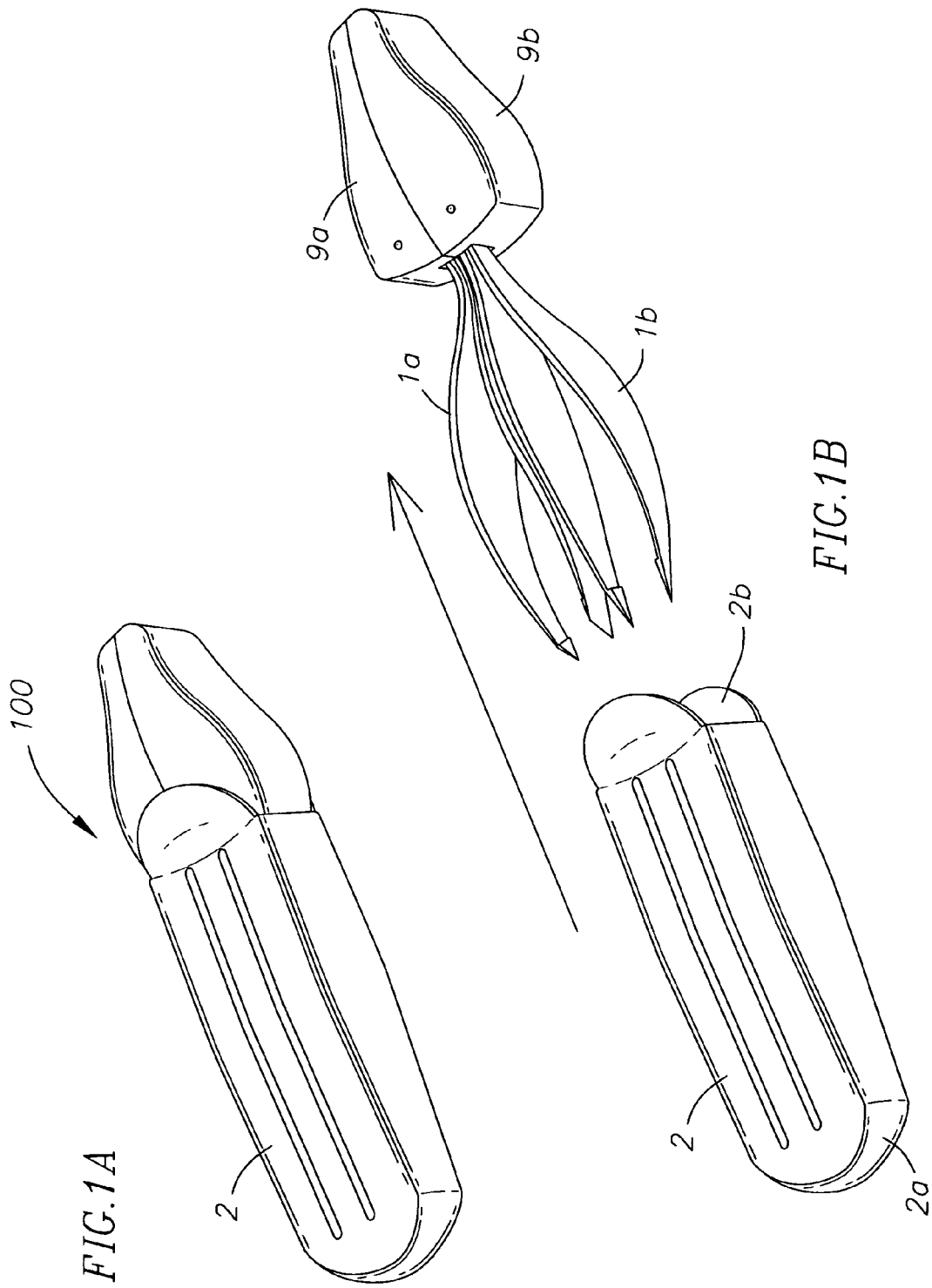
Figure 2:
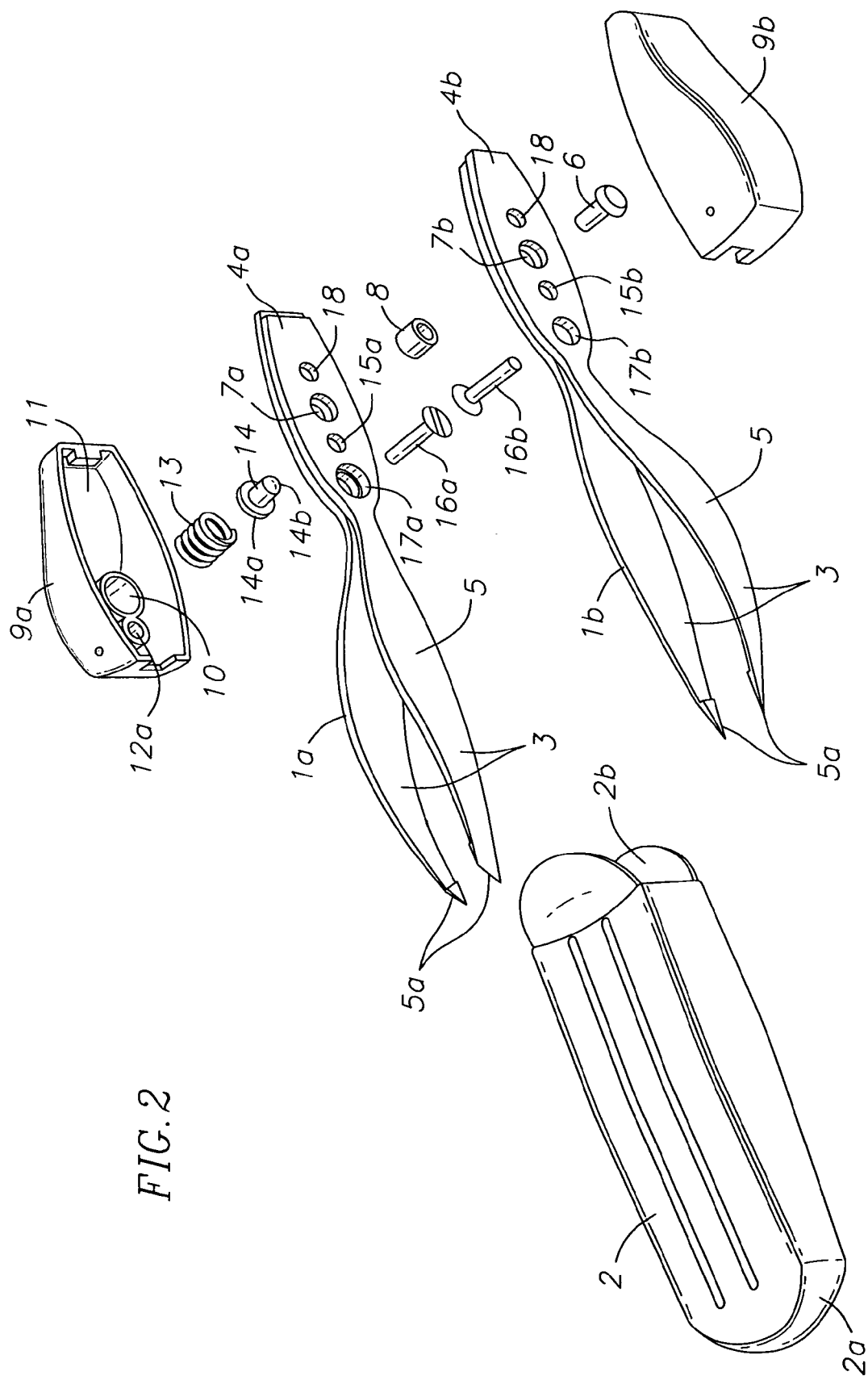
FIG. 2 shows the components of the compact double tweezers.

FIG. 1A shows the fully encased compact double tweezers device 100 of this invention. As shown in FIG. 1B, there are two tweezers 1a and 1b joined together side by side. The tweezers slip into a cover or cap 2 for storage when not in use. This device, as shown in FIG. 1A, is compact and portable and if desired, it can be adopted to hang on a chain or a necklace and other similar devices by simply attaching a ring 19 as shown in FIG. 1C on top of the closed end 2a of the cover 2, opposite the opened end 2b where the tweezer head section 3 slips into. Each tweezers here has a tweezer head section 3 extending to a base section 4 constructed from two elongated flat sheets fused together at the base section 4 which consequently forms a freely moving tweezer head section at the opposite end which could be linear or curved. One tweezers' base section is labeled 4a and the other 4b. FIG. 2 shows the components of this device 100. To be able to fold and unfold the tweezers as shown in FIGS. 1B and 4, a series of connectors are required.

The tweezer head section 3 includes the pincers 5 which are spaced apart, consequently, allowing movement at this end as pressure by the fingers for example, is exerted or released at its outside surfaces. It is this end that picks up and releases an object as the pincers close together or separate apart, respectively. The tip 5a is at the end of the pincers opposite the section extending to the base section 4.

Figure 3:
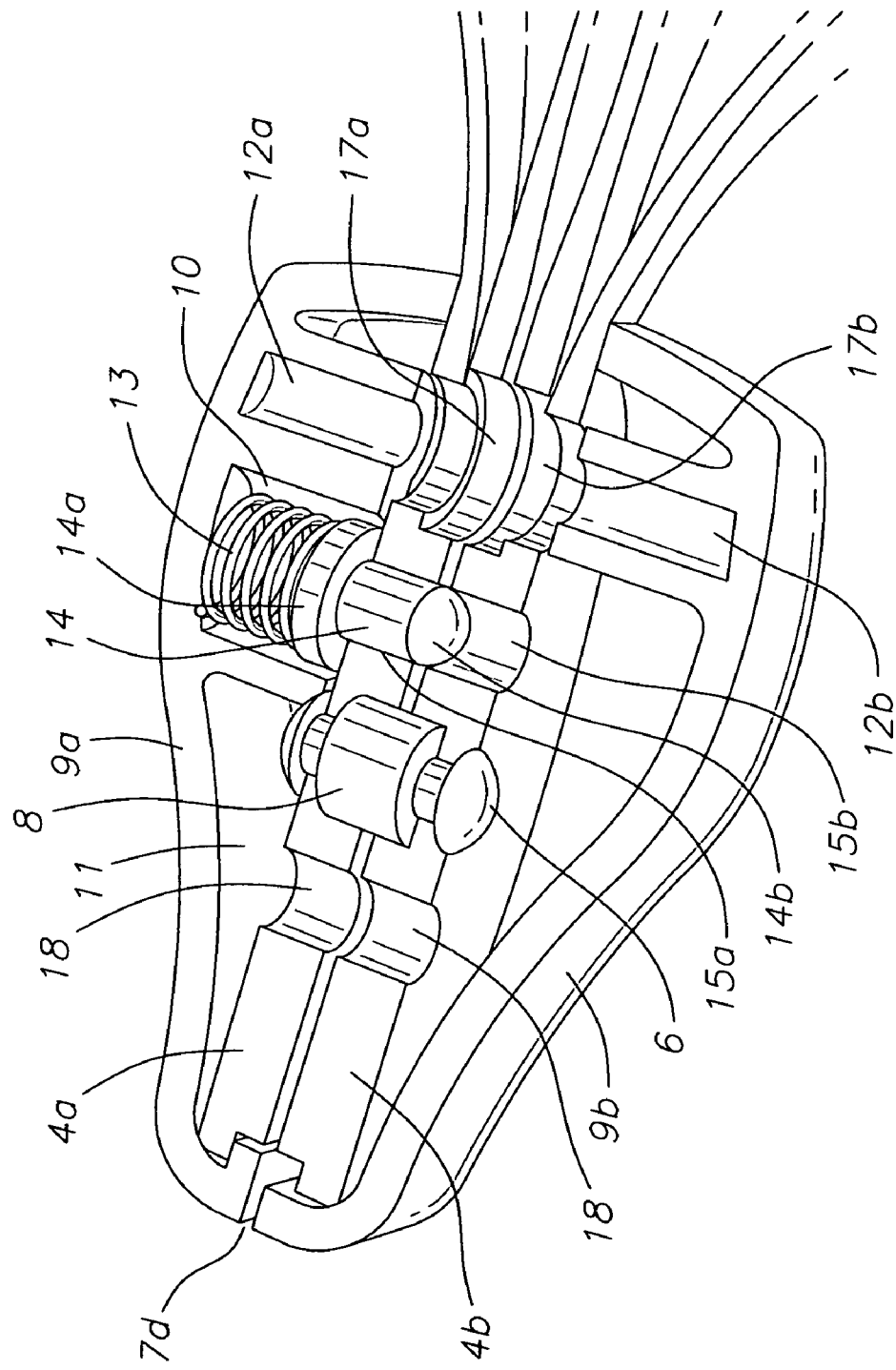

To assemble, a rivet or a connector with threads at opposite ends hereinafter referred to as central connector 6 is introduced into the central holes 7a and 7b placing a liner 8 in between, that is, one end of the central connector enters hole 7a of one tweezers, inserts a liner 8, and exits through hole 7b of the other tweezers. The direction of insertion can be reversed. To keep the liner 8 from moving along the central connector and the passage formed when hole 7a and hole 7b align with each other, the inserted liner used has an outside surface diameter larger than the central connector 6 as shown in FIGS. 3 and 3A and both holes 7a and 7b widens onto a larger hole 7c to form a central wider trough after alignment to accommodate and house the liner as shown in FIG. 3A. The walls of the wider trough keep the liner in place. If the connector is one with threads on each end, the two tweezers are connected to each other by placing an internally threaded connector such as a nut at each end of the central connector. If it is a rivet as shown in FIG. 3, the second head is pressed after the rivet passes through the central holes 7a and 7b. Other connectors can be used so long as it does the function stated here. FIG. 3 shows the position of the rivet with the liner 8. The distance between the two heads of the rivets or the position of the nuts at both end of the connectors determine the size of the gap 7d between the two tweezers. The size of the gap 7d is determined by the difference between the distance between the heads of the rivets or nuts and the length of the combined thickness of the base sections 4a and 4b. The gap should just be enough to allow one tweezers to easily pivot or turn relative to the other tweezers without causing the tweezers to rub against each other and also accommodate the height of the tip of the locator pin which temporarily locks the tweezers on a position as would be described later. After the two tweezers are connected to each other, one tweezer is rotated at approximately 90 degrees so that one is directed horizontally while the other is directed vertically. Each base sections of the two tweezers have an external base cover 9. One of the base cover 9a has an enclosed cylindrical channel 10 like a boss protruding from an inner surface of 11 of the base cover. The other base cover 9b does not have this channel as shown in FIG. 3. Both base covers, however, have a second channel 12a and 12b located most proximal to the tweezer head section as shown in FIGS. 2 and 3. Channel 10 has a bigger diameter than channels 12 to accommodate a spring 13. After the spring is applied into channel 10, a locator pin 14 having an annular stopper 14a on one end and a rounded tip 14b on the other end is situated on top of the spring with the annular stopper pressing or engaging with the exposed end of the spring as shown in FIG. 3. The annular stopper has a protruding cylindrical piece 14c extending inside the top of and enveloped by the spring. Instead of an annular stopper as described above, this can just be a flat circular head as shown in FIG. 3. The locator pin 14 is inserted on hole 15a proximal to channel 12a with the annular stopper situating on top of the exposed end of the spring 13 and while in this position, a connector 16a fastens base cover 9a to one of the tweezers 1a through opening 17a into channel 12a. After fastening one of the tweezers through base section 4a to one of the base cover 9a, the rounded tip 14b of the locator pin protrudes from hole 15a on base section 4a. It is recommended to attach base cover 9a before attaching base cover 9b to the other tweezers 1b. Attaching base cover 9b to tweezers 1b is simply done by inserting a second connector 16b to channel 12b through opening 17b on base section 4b. The connector 16 can be a screw but other similar connectors can be used. FIG. 5 shows the assembled tweezers perpendicular to each other. The above assembly is facilitated when the tweezers are positioned at approximately 90 degrees because the second tweezers would not be on the way while the spring and locator pin are installed on channel 10 and hole 15a, respectively. After the base covers are attached to the respective base sections of the tweezers, the tweezers are free to pivot or rotate at any angle in relation to each other. The base covers 9 serve as the handle for the tweezers.

However, it is important to firmly hold the tweezers when it is in the folded position during storage and especially when it is fully unfolded during usage to prevent it from turning inadvertently. The locator pin 14 locks the tweezers in the folded and unfolded position. In a folded position, the rounded tip 14b of the locator pin protruding from hole 15a of the first tweezer base section 4a inserts into hole 15b which is aligned with hole 15a but located on the base section 4b of the other tweezers as shown in FIG. 3. Because the rounded tip 14b inserts into hole 15b, one tweezers is prevented from easily turning or unfolding on its own. To position the tweezers from the folded position to a fully unfolded position where the tips of the tweezers are on opposite sides as shown in FIG. 4, a slight twisting pressure is exerted on the base cover to unfold the tweezers. The pressure on the rounded tip 14b plus the twisting action on the base covers causes the rounded tip 14b to hit the inside side walls of hole 15b which causes the rounded tip 14b of the locator pin to recede towards hole 15a due to the translation of the pressure from the tip 14b to the locator pin's annular stopper pressing on the spring 13 which compresses the spring. The arch on the tip also facilitates the withdrawal of the rounded tip from hole 15b, consequently, only the rounded tip of the locator pin should enter hole 15b. The rounded tip 14b stays recessed or regressed until it encounters another hole 18 such as one located at the end of the base section of the tweezers, most distal to the tweezer head section. At this point, rounded tip 14b enters hole 18 which causes the annular stopper to release the pressure on the spring. Tip 14b is at hole 18 when the tweezers are in the fully unfolded position as shown in FIG. 4. With the rounded tip 14b inside hole 18, the tweezers are stabilized in the unfolded position thereby preventing rotational movement of the tweezers during usage. This action of the rounded tip 14b switching back and forth between 15b and 18 is repeated whenever the tweezers fold and unfolds. The small letters a, b, etc. are used when there is a need to differentiate the same part on the two tweezers for example, with one tweezers designated with the small letter a and the other with the small letter b or sometimes for sections within a part, for example, 4 is represented by 4a and 4b; 9 is represented by 9a and 9b; 12 is represented by 12a and 12b and 16 is represented by 16a and 16b.

However, it is important to firmly hold the tweezers when it is in the folded position during storage and especially when it is fully unfolded during usage to prevent it from turning inadvertently. The locator pin 14 locks the tweezers in the folded and unfolded position. In a folded position, the rounded tip 14b of the locator pin protruding from hole 15a of the first tweezer base section 4a inserts into hole 15b which is aligned with hole 15a but located on the base section 4b of the other tweezers as shown in FIG. 3. Because the rounded tip 14b inserts into hole 15b, one tweezers is prevented from easily turning or unfolding on its own. To position the tweezers from the folded position to a fully unfolded position where the tips of the tweezers are on opposite sides as shown in FIG. 4, a slight twisting pressure is exerted on the base cover to unfold the tweezers. The pressure on the rounded tip 14b plus the twisting action on the base covers causes the rounded tip 14b to hit the inside side walls of hole 15b which causes the rounded tip 14b of the locator pin to recess towards hole 15a due to the translation of the pressure from the tip 14b to the locator pin's annular stopper pressing on the spring 13 which compresses the spring. The arch on the tip also facilitates the withdrawal of the rounded tip from hole 15b, consequently, only the rounded tip of the locator pin should enter hole 15b. The rounded tip 14b stays recessed until it encounters another hole 18 such as one located at the end of the base section of the tweezers, most distal to the tweezer head section. At this point, rounded tip 14b enters hole 18 which causes the annular stopper to release the pressure on the spring. Tip 14b is at hole 18 when the tweezers are in the fully unfolded position as shown in FIG. 4. With the rounded tip 14b inside hole 18, the tweezers are stabilized in the unfolded position thereby preventing rotational movement of the tweezers during usage. This action of the rounded tip 14b switching back and forth between 15b and 18 is repeated whenever the tweezers fold and unfolds. The small letters a, b, etc. are used when there is a need to differentiate the same part on the two tweezers for example, with one tweezers designated with the small letter a and the other with the small letter b or sometimes for sections within a part.

While the embodiments of the present invention have been described, it should be understood that various changes, adaptations, and modifications may be made therein without departing from the spirit of the invention and the scope of the claims.

I claim:

1. A compact tweezers having two tweezers in a folding and unfolding positions, comprising:
   two tweezers, each having a head section including a pincer and a pair of tips and a base section having several holes, a central hole having a central connector disposed within, the central connector connecting the two tweezers and allowing the tweezers to rotate relative to each other, a plurality of holes accommodating a locator pin for locking the tweezers in a folded and unfolded position, and a hole having a connector disposed within for fastening a base cover to each tweezers
   the base covers serving as handles for the tweezers; and,
   means for positioning the two tweezers back and forth from the folding position to the unfolding position.

2. The compact tweezers of claim 1 wherein the two tweezers are positioned back and forth from a folding to an unfolding position by the locator pin inserted into a first hole, the locator pin having a rounded tip on one end protruding from the first hole and inserting into a second hole when the two tweezers are in one position and an annular stopper on another end situated on top of a spring inside a channel, the annular stopper having a diameter greater than the turn diameter of the spring pressing and compressing the spring when the rounded tip recedes towards the hole as the tweezers change position and releasing the spring when the rounded tip enters into a third hole when the two tweezers situate in another position.

3. The compact tweezers of claim 2 wherein the annular stopper has a protruding cylindrical piece opposite the rounded tip.

4. The compact tweezers of claim 2 wherein the annular stopper is a flat circular head.

5. The compact tweezers of claim 2 wherein the hole where the rounded tip inserts into aligns with the hole from where the rounded tip protrudes from.

6. The compact tweezers of claim 2 wherein the tweezers change position when a twisting pressure is exerted on the external covers of each tweezers.

7. The compact tweezers of claim 1 further comprising a cover for shielding the head sections of the two tweezers.

8. The compact tweezers of claim 1 further comprising a ring attached to a closed end top of a cover shielding the head sections of the two tweezers.

9. The compact tweezers of claim 1 further comprising a liner at a mid section of the central connector having an outside surface diameter greater than the central connector, the liner situating on a trough to keep the liner from moving along the central connector, the central connector forming a gap between the two tweezers to keep the tweezers from rubbing each other.

10. A compact tweezers having two tweezers in a folding and unfolding positions, comprising:
    two tweezers, each having a head section including a pincer and a pair of tips and a base section having several holes;
    a central connector connecting the two tweezers and allowing the tweezers to rotate relative to each other;

an external base cover for each base section of the tweezers, the external base covers serving as handles for the tweezers; and, a locator pin inserted into a hole, the locator pin having a rounded tip on one end protruding from the hole and inserting into a second hole when the two tweezers are in one position and an annular stopper on another end situated on top of a spring inside a channel, the annular stopper having a diameter greater than the turn diameter of the spring pressing and compressing the spring when the rounded tip recedes towards the hole as the tweezers change position and releasing the spring when the rounded tip enters into a third hole when the two tweezers situate in another position.

11. The compact tweezers of claim 10 further comprising a cover for shielding the head sections of the two tweezers.

12. The compact tweezers of claim 10 further comprising a ring attached to a closed end top of a cover shielding the head sections of the two tweezers.

13. The compact tweezers of claim 10 further comprising a liner at a mid section of the central connector having an outside surface diameter greater than the central connector, the liner situating on a trough to keep the liner from moving along the central connector, the central connector forming a gap between the two tweezers to keep the tweezers from rubbing each other and for accommodating the protruding rounded tip of the locator pin.

14. The compact tweezers of claim 10 wherein the annular stopper has a protruding cylindrical piece opposite the rounded tip.

15. The compact tweezers of claim 10 wherein the annular stopper is a flat circular head.

16. The compact tweezers of claim 10 wherein the hole where the rounded tip inserts into aligns with the hole from where the rounded tip protrudes from.

17. The compact tweezers of claim 10 wherein the tweezers change position when a twisting pressure is exerted on the external covers of the tweezers.

18. A compact tweezers having two tweezers in a folding and unfolding positions, comprising:

two tweezers, each having a head section including a pincer and a pair of tips and a base section having several holes;

a central connector connecting the two tweezers having a liner at a mid section of the central connector, the liner having an outside surface diameter greater than the central connector and situating on a trough to keep the liner from moving along the central connector, the central connector forming a gap between the two tweezers to keep the tweezers from rubbing each other as the tweezers rotate relative to each other and for accommodating a protruding rounded tip on a locator pin;

an external base cover for each base section of the tweezers, the external base covers serving as handles for the tweezers;

a locator pin inserted into a hole, the locator pin having the rounded tip on one end protruding from the hole and inserting into a second hole when the two tweezers are in one position and an annular stopper on another end situated on top of a spring inside a channel, the annular stopper having a diameter greater than the turn diameter of the spring pressing and compressing the spring when the rounded tip recedes towards the hole as the tweezers change position and releasing the spring when the rounded tip enters into a third hole when the two tweezers situate in another position; and, a cover for shielding the head sections of the two tweezers.

19. The compact tweezers of claim 18 wherein the annular stopper has a protruding cylindrical piece opposite the rounded tip.

20. The compact tweezers of claim 18 wherein the annular stopper is a flat circular head.

* * * * *